US00PP33913P2

(12) United States Plant Patent
van Langen

(10) Patent No.: US PP33,913 P2
(45) Date of Patent: Jan. 25, 2022

(54) ***ECHEVERIA* PLANT NAMED 'AMIECH2003'**

(50) Latin Name: ***Echeveria* hybrid**
Varietal Denomination: AMIECH2003

(71) Applicant: Novoami B.V., Heerhugowaard (NL)

(72) Inventor: Gerard van Langen, Heerhugowaard (NL)

(73) Assignee: Novoami B.V., Heerhugowaard (NL)

( * ) Notice: Subject to any disclaimer, the term of this patent is extended or adjusted under 35 U.S.C. 154(b) by 0 days.

(21) Appl. No.: 17/300,672

(22) Filed: Sep. 21, 2021

(30) Foreign Application Priority Data

Nov. 25, 2020 (QZ) ..... PBR 2020/2979

(51) Int. Cl.
*A01H 5/02* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Echeveria* plant named 'AMIECH2003' which is characterized by somewhat relaxed foliage held in a compact basal rosette, an adaxial foliar surface with a dark green general appearance, an abaxial foliar surface that becomes progressively suffused with greyed-purple as leaves age, mature foliage that is tipped and narrowly margined with greyed-orange on the adaxial surface and greyed-purple on the abaxial surface, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'AMIECH2003'.

CROSS REFERENCE TO RELATED APPLICATIONS

This application claims priority to the Community Plant Variety Rights application number 2020/2979, filed Nov. 25, 2020, which is herein incorporated by reference.

BACKGROUND OF THE INVENTION

Parentage: 'AMIECH2003' is an interspecific hybrid seedling selection resulting from the controlled pollination of an unnamed *Echeveria elegans* plant (not patented), the seed parent, with an unnamed *Graptopetalum filiferum* plant (not patented), the pollen parent. The crossing was made by the inventor in the summer of 2017 at a commercial greenhouse in Heerhugowaard, the Netherlands. In the autumn of 2018, one seedling was observed which exhibited unique growth and foliage characteristics. The seedling was isolated for further evaluation in order to confirm the distinctness and stability of the characteristics first observed. Upon confirmation of distinctness and stability, 'AMIECH2003' was selected for commercialization.

Asexual Reproduction: Asexual reproduction of the new cultivar 'AMIECH2003', by way of rooting leaf cuttings, was first initiated in the spring of 2019 at the inventor's commercial greenhouse in Heerhugowaard, the Netherlands.

Through two subsequent generations, the unique features of this cultivar have proven to be stable and true to type.

SUMMARY OF THE INVENTION

The cultivar 'AMIECH2003' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2003'. These characteristics in combination distinguish 'AMIECH2003' as a new and distinct *Echeveria* hybrid cultivar:

1. 'AMIECH2003' exhibits a compact basal rosette; and
2. 'AMIECH2003' exhibits foliage with a somewhat relaxed attitude; and
3. 'AMIECH2003' exhibits obovate foliage with a mucronate apex; and
4. 'AMIECH2003' exhibits an adaxial foliar surface with a dark green general appearance; and
5. 'AMIECH2003' exhibits an abaxial foliar surface which becomes progressively suffused with greyed-purple as leaves age; and
6. 'AMIECH2003' exhibits mature foliage that is tipped and narrowly margined with greyed-orange on the adaxial surface and tipped with greyed-purple on the adaxial surface.

BOTANICAL DESCRIPTION OF THE PLANT

Figure 1:
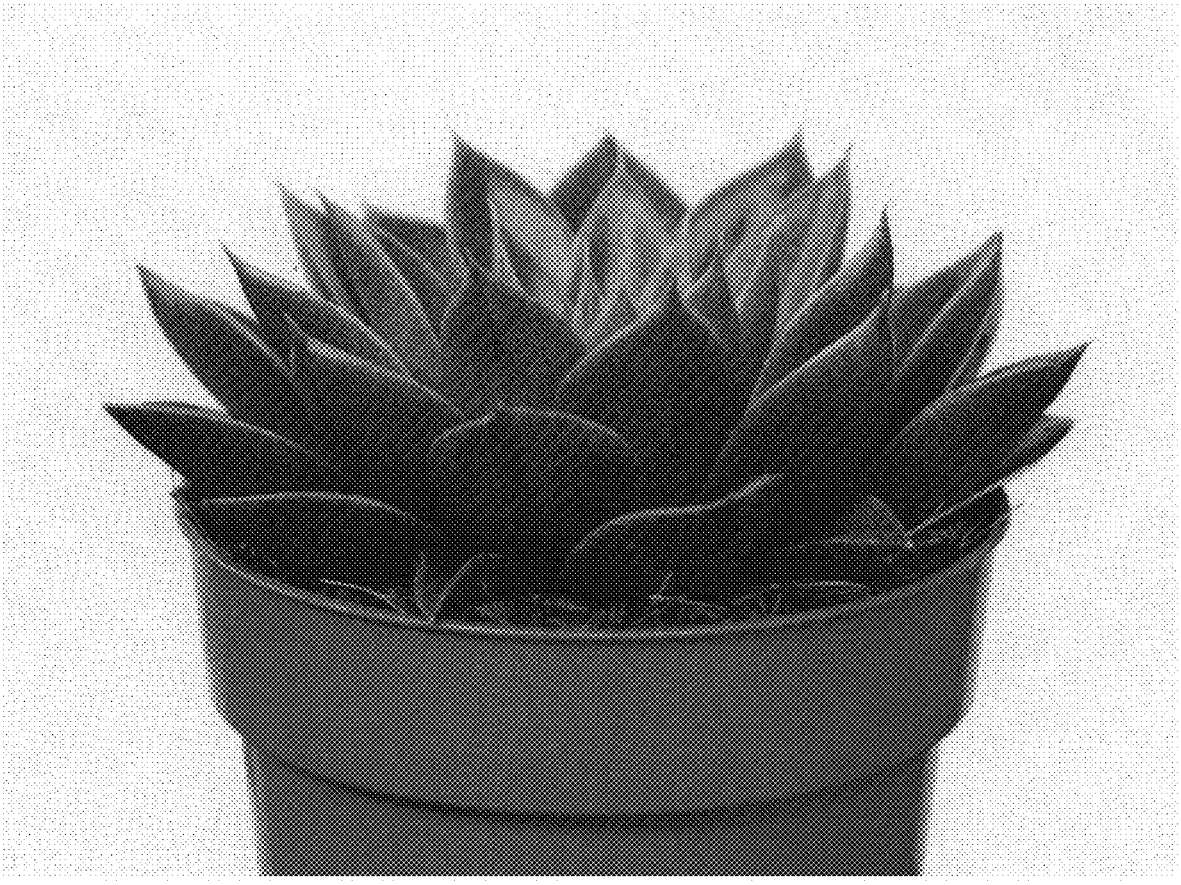
FIG. 1 illustrates, as nearly true as it is reasonably possible to make the same in color photographs of this type, an exemplary plant of 'AMIECH2003' grown in a commercial greenhouse in Heerhugowaard, the Netherlands. This plant is approximately 26 week-old, shown planted in an 8.5 cm container.
Figure 2:
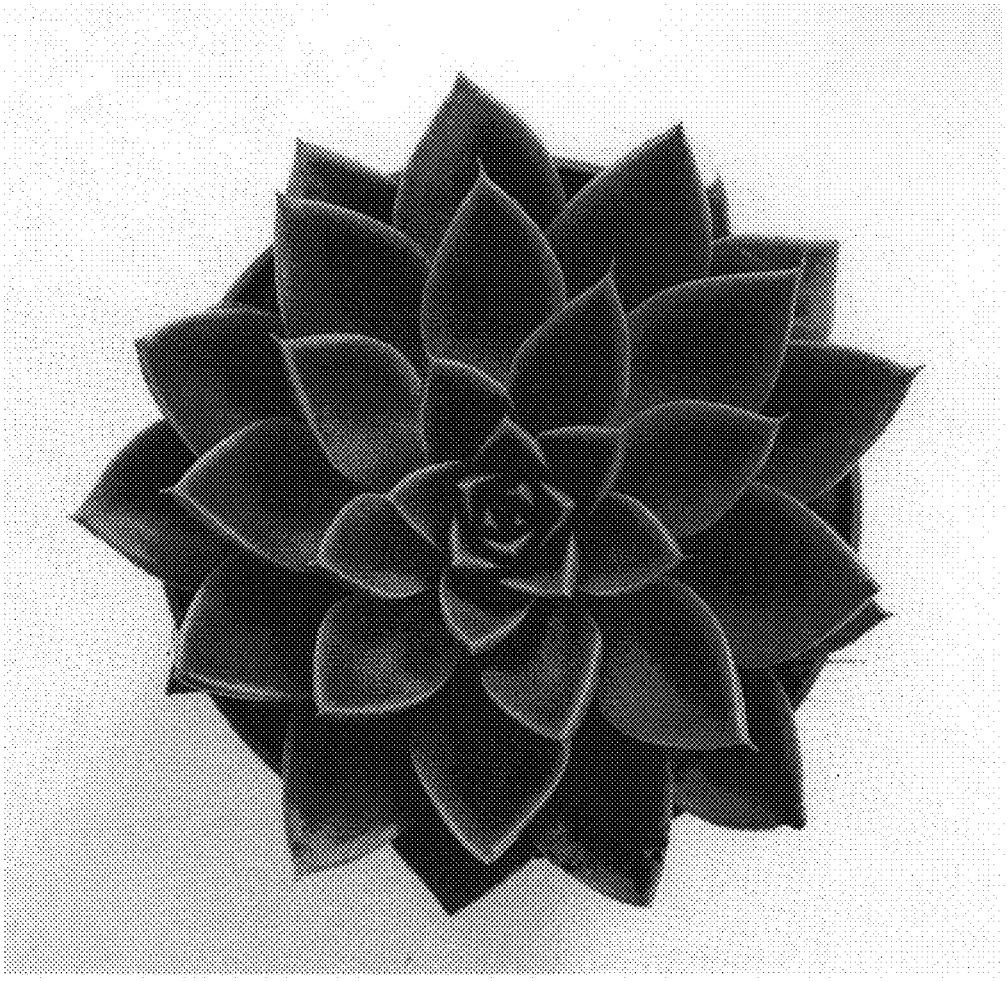
FIG. 2 illustrates, as nearly true as it is reasonably possible to make the same in color photographs of this type, the typical foliage arrangement of 'AMIECH2003'.
Figure 3:
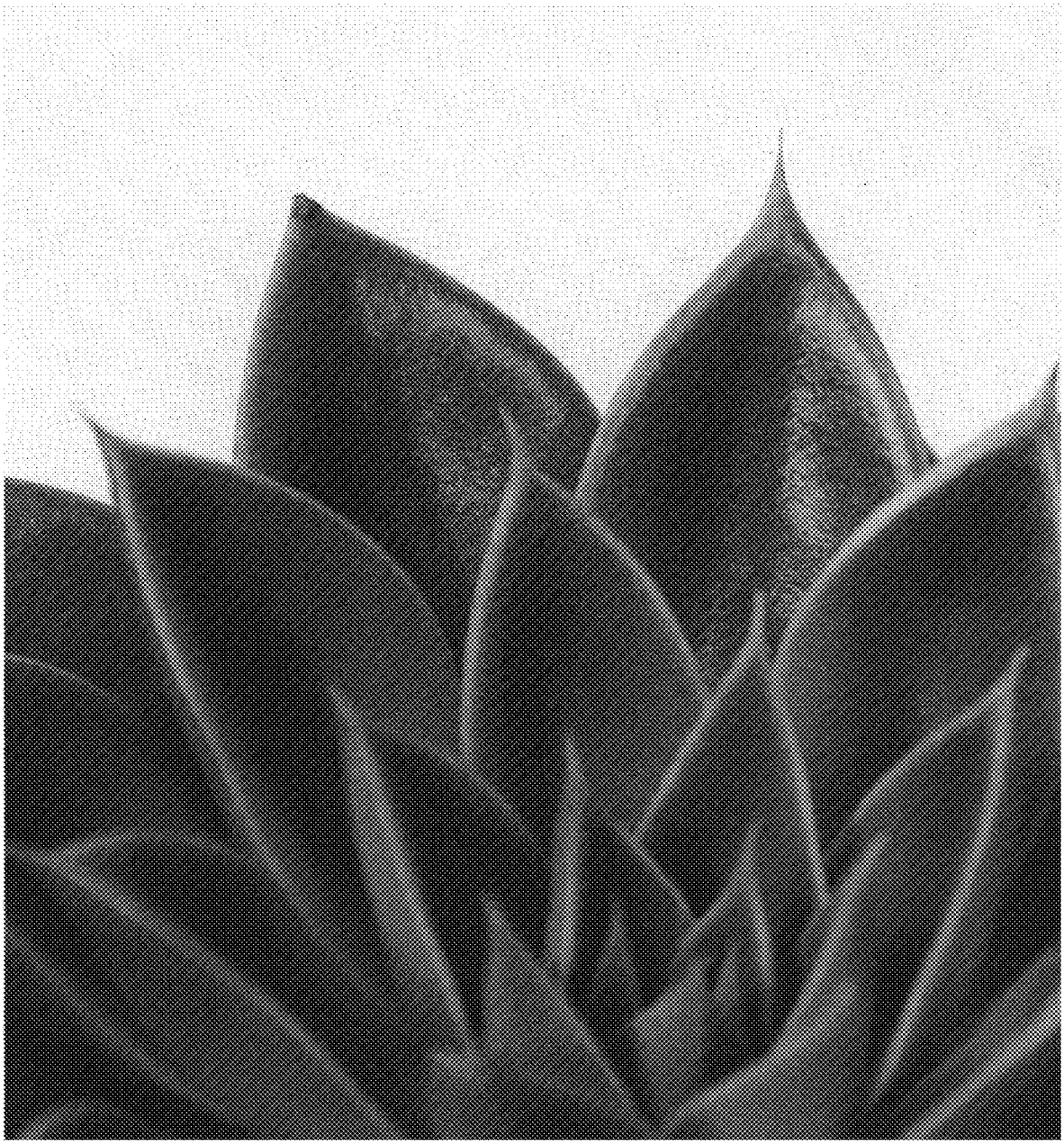
FIG. 3 illustrates, as nearly true as it is reasonably possible to make the same in color photographs of this type, the adaxial surface of the mature foliage 'AMIECH2003'.
Figure 4:
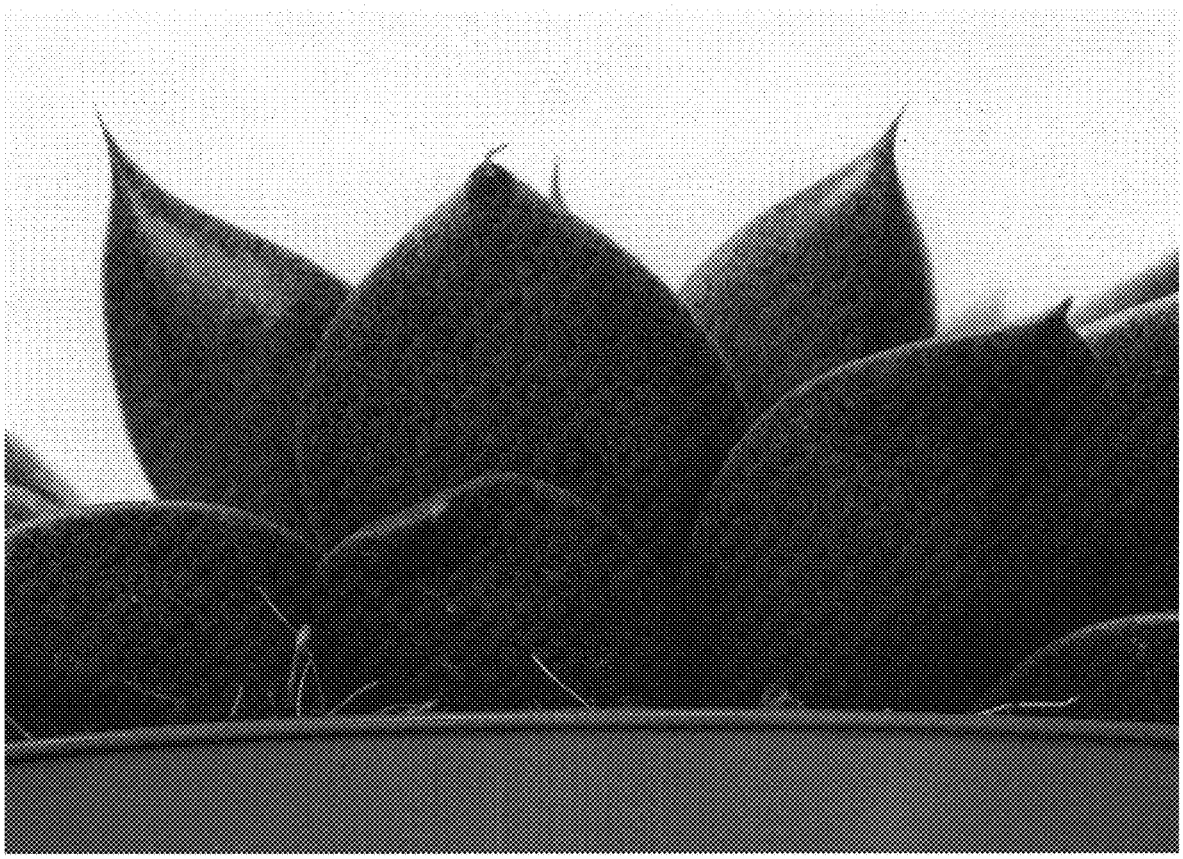
FIG. 4 illustrates, as nearly true as it is reasonably possible to make the same in color photographs of this type, the abaxial surface of the mature foliage 'AMIECH2003'.

The following observations and measurements made in May of 2021 describe averages from a sample set of six specimens of 26 week-old 'AMIECH2003' plants grown in 8.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2003' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2003' and comparisons with the parent plants and closest known comparator are provided below.

Plant description:

*Growth habit*.—Succulent perennial with foliage growing in a non-branched basal rosette.

*Plant shape*.—Flattened.

*Height from soil level to top of foliar plane*.—4.0 cm.

*Plant spread*.—Average of 10.3 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in an 8.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 40 leaves per rosette.

*Shape*.—Obovate.

*Dimensions*.—4.7 cm long, 1.9 cm wide, and 0.5 cm thick, on average.

*Aspect*.—Moderately concave.

*Attitude*.—Juvenile foliage at the center of the rosette is held upright; foliage becomes progressively more relaxed towards the outer whorls of mature foliage.

*Apex*.—Mucronate.

*Base*.—Cuneate.

*Margin*.—Entire; margins are not undulate.

*Pubescence, texture and luster of the adaxial surface*.—Smooth, glabrous, and glossy.

*Pubescence, texture and luster of the abaxial surface*.—Smooth, glabrous, and moderately glossy.

*Luster of the adaxial surface*.—Moderately glossy.

*Luster of the abaxial surface*.—Moderately glossy.

*Color*.—Juvenile foliage, adaxial surface — Green, nearest to a RHS 137B; narrowly margined with greyed-green, nearest to RHS 194B; tipped with greyed-green, nearest to RHS 195B. Juvenile foliage, abaxial surface — Nearest to a mixture of green and greyed-green, RHS 138B and 191A; narrowly margined with greyed-green, nearest to RHS 194B; tipped with greyed-green, nearest to RHS 195B. Mature foliage, adaxial surface — Green, nearest to RHS NN137B; narrowly margined greyed-green, nearest to a mixture of RHS 195A and 195B; margins are lightly suffused with greyed-orange towards the margins, nearest to a mixture of RHS 174B and 174C; tipped with greyed-orange, nearest to a mixture of RHS 174B and 174C. Mature foliage, abaxial surface — Yellow-green, nearest to RHS 148C, and moderately to strongly suffused with greyed-purple, nearest to RHS 184A; lamina is further suffused with a mixture of greyed-green and brown towards the apex, nearest to RHS 197A and 200B; tipped with greyed-purple, nearest to RHS 184A. Venation, adaxial surface — No visible venation. Venation, abaxial surface — No visible venation.

*Petiole*.—No petiole; leaves are sessile.

Inflorescence: No flowering has been observed to date.

COMPARISONS WITH THE PARENT PLANTS AND CLOSEST KNOWN COMPARATOR

Plants of the new cultivar 'AMIECH2003' differ from the seed parent, an unnamed *Echeveria elegans* plant (not patented), in the following characteristics described in Table 1 below.

TABLE 1

| Characteristic | 'AMIECH2003' | The seed parent. |
|---|---|---|
| Foliage thickness. | Thinner than the seed parent. | Thicker than 'AMIECH2003'. |
| Foliage apex. | Mucronate. | Apiculate. |
| General coloration of the adaxial foliar surface. | Green. | Light blue-green. |

Plants of the new cultivar 'AMIECH2003' differ from the pollen parent, an unnamed *Graptopetalum filiferum* plant (not patented), in the following characteristics described in Table 2 below.

TABLE 2

| Characteristic | 'AMIECH2003' | The pollen parent. |
|---|---|---|
| Foliage size. | Larger than the pollen parent. | Smaller than 'AMIECH2003'. |
| General coloration of the adaxial foliar surface. | Green. | Greyed-green. |

COMPARISONS WITH THE CLOSEST KNOWN COMPARATOR

Plants of the new cultivar 'AMIECH2003' differ from the closest known commercial comparator, the species *Echeveria agavoides* 'Mexicana' (not patented), in the following characteristics described in Table 3 below.

TABLE 3

| Characteristic | 'AMIECH2003' | 'Mexicana' |
|---|---|---|
| Plant size. | Smaller than 'Mexicana'. | Larger than 'AMIECH2003'. |
| Growth habit. | More compact, relative to 'Mexicana'. | Less compact, relative to 'AMIECH2003'. |
| Foliage aspect. | Not curled upward at the apex. | Curled upward at the apex. |
| General coloration of the adaxial foliar surface. | Darker green, relative to 'Mexicana'. | Lighter green, relative to 'AMIECH2003'. |

That which is claimed is:

1. A new and distinct variety of *Echeveria* hybrid plant named 'AMIECH2003', substantially as described and illustrated herein.

* * * * *